United States Patent [19]

Martindale et al.

[11] Patent Number: 4,724,271

[45] Date of Patent: Feb. 9, 1988

[54] REGENERATION OF DEHYDROCYCLODIMERIZATION CATALYST

[75] Inventors: David C. Martindale, Roselle; Joseph A. Kocal, Gurnee; Tai-Hsiang Chao, Mt. Prospect, all of Ill.

[73] Assignee: UOP Inc., Des Plaines, Ill.

[21] Appl. No.: 33,136

[22] Filed: Mar. 31, 1987

Related U.S. Application Data

[60] Continuation-in-part of Ser. No. 871,968, Jun. 9, 1986, Pat. No. 4,654,455, which is a division of Ser. No. 806,984, Dec. 9, 1985, Pat. No. 4,636,483.

[51] Int. Cl.$^4$ ............................................. C07C 12/02
[52] U.S. Cl. ...................................... 585/415; 502/47
[58] Field of Search ........................... 585/415; 502/47

[56] References Cited

U.S. PATENT DOCUMENTS

| | | | |
|---|---|---|---|
| 3,386,801 | 6/1968 | Kuehl | 502/61 |
| 3,507,778 | 4/1970 | Gladrow et al. | 502/64 |
| 4,225,419 | 9/1980 | Myers | 208/135 |
| 4,350,835 | 9/1982 | Chester et al. | 502/61 |
| 4,463,209 | 7/1984 | Kursewicz et al. | 585/467 |
| 4,477,582 | 10/1984 | Miale | 502/26 |
| 4,567,152 | 1/1986 | Pine | 502/64 |
| 4,590,323 | 5/1986 | Chu | 585/417 |
| 4,600,700 | 7/1986 | McHale | 502/50 |
| 4,642,407 | 2/1987 | Dessau et al. | 585/640 |

FOREIGN PATENT DOCUMENTS 2117367 10/1983 United Kingdom ................ 502/61

Primary Examiner—Curtis R. Davis
Attorney, Agent, or Firm—Thomas K. McBride; John F. Spears, Jr.; Richard J. Cordovano

[57] ABSTRACT

A process for catalytic dehydrocyclodimerization and regeneration of the catalyst. $C_2$ to $C_5$ aliphatic hydrocarbons are reacted to produce aromatics, using a water-sensitive catalyst of a composition especially adapted to minimize deposition of coke on the catalyst. The catalyst is comprised of alumina which contains phosphorus, gallium, and a crystalline aluminosilicate having a silica to alumina ratio of at least 12. The use of this catalyst has resulted in a five-fold reduction in the rate of coke deposition, compared to a conventional dehydrocyclodimerization catalyst. However, the activity of this catalyst is significantly reduced by exposure to water at the temperatures normally used in removing the coke, which is accomplished by burning the coke in a combustion zone in the presence of oxygen, producing carbon dioxide and water. At least a portion of the gas leaving the combustion zone catalyst bed is combined with air and recycled back to the combustion zone. This mode of operation causes the concentration of water in the recycled stream to increase to an unacceptable value. Therefore, to obtain the benefit of this superior catalyst, it is necessary to utilize water removal steps in the catalyst regeneration procedure.

4 Claims, 3 Drawing Figures

REGENERATION OF DEHYDROCYCLODIMERIZATION CATALYST

CROSS-REFERENCE TO RELATED APPLICATION

This is a continuation-in-part of co-pending application Ser. No. 871,968, filed June 9, 1986, now U.S. Pat. No. 4,654,455, which is dated Mar. 31, 1987 Ser. No. 871,968 is a divisional of Ser. No. 806,984 filed Dec. 9, 1985 now U.S. Pat. No. 4,636,483 which is dated Jan. 31, 1987.

FIELD OF THE INVENTION

This invention relates to the field of hydrocarbon conversion processes in which a catalyst is utilized. More specifically, it relates to the regeneration of hydrocarbon conversion catalyst after the catalyst has been used.

BRIEF SUMMARY OF THE INVENTION

The present invention is a process for catalytic dehydrocyclodimerization and regeneration of the catalyst. $C_2$ to $C_5$ aliphatic hydrocarbons are reacted to produce aromatics, using a water-sensitive catalyst of a composition especially adapted to minimize deposition of coke on the catalyst. The catalyst is comprised of alumina which contains phosphorus, gallium, and crystalline aluminosilicate having a silica to alumina ratio of at least 12. The use of this catalyst has resulted in a five-fold reduction in the rate of coke deposition, compared to a conventional dehydro-cyclodimerization catalyst. However, the activity of this catalyst is significantly reduced by regenerating it in a conventional manner. Such regeneration results in exposure to water at the temperatures normally used in removing coke. Coke removal is accomplished by burning it in the presence of oxygen in a combustion zone, producing carbon dioxide and water. At least a portion of the gas leaving the combustion zone catalyst bed is combined with air and recycled back to the combustion zone. This mode of operation causes the concentration of water in the recycled stream to increase to an unacceptable value. Therefore, to obtain the benefit of this superior catalyst, it is necessary to utilize water removal steps in the catalyst regeneration procedure.

In a broad embodiment, the present invention is a process for the dehydrocyclodimerization of hydrocarbons which comprises contacting a feed stream containing aliphatic hydrocarbons with a catalyst, under dehydrocyclodimerization conditions, where said catalyst is comprised of phosphorus-containing alumina, a gallium component, and crystalline aluminosilicate having a silica to alumina ratio of at least 12, where said catalyst becomes deactivated as a result of the dehydrocyclodimerization reaction, and where water is excluded from contact with said catalyst during catalyst regeneration, the catalyst regeneration procedure being comprised of the steps of: passing spent catalyst through a combustion zone which is maintained at a coke-oxidizing temperature, wherein said spent catalyst is contacted with a dry recycle gas comprising oxygen; withdrawing a flue gas stream from the combustion zone; mixing an air stream with said flue gas stream to form said recycle gas stream; passing the recycle gas stream through a drying zone wherein water is removed from the recycle gas stream; and, passing the dry recycle gas stream through the catalyst in the combustion zone.

In another embodiment, the present invention comprises passing spent catalyst through a combustion zone which is maintained at a coke-oxidizing temperature, wherein said spent catalyst is contacted with a dry recycle gas comprising oxygen; passing catalyst leaving said combustion zone through a catalyst drying zone wherein water is removed from the catalyst; passing a first air stream through an air drying zone wherein water is removed from said first air stream and heating said first air stream; passing at least a portion of said heated and dried first air stream through said catalyst drying zone in contact with catalyst, thereby removing water from the catalyst; mixing at least a portion of the air stream leaving the catalyst drying zone with a gas stream leaving the catalyst bed in the combustion zone to form a flue gas stream; mixing a second air stream with said flue gas stream to form said recycle gas stream; passing the recycle gas stream through a drying zone wherein water is removed from the recycle gas stream; and, passing the dry recycle gas stream through the catalyst in the combustion zone.

BACKGROUND OF THE INVENTION

Dehydrocyclodimerization is a reaction where reactants comprising paraffins and olefins containing from 2 to 5 carbon atoms per molecule are reacted in the presence of a catalyst to produce aromatics, with $H_2$ and light ends as by-products. This process is quite different from the more conventional reforming or dehydrocyclization processes where $C_6$ and higher carbon number reactants, primarily paraffins and naphthenes, are converted to aromatics. Aromatics formed in these conventional processes contain the same or a lesser number of carbon atoms per molecule as compared to the reactants from which they were formed, indicating the absence of dimerization reactions. In contrast, the dehydrocyclodimerization reaction results in an aromatic product that always contains more carbon atoms per molecule than the $C_2$ to $C_5$ reactants, thus indicating that the dimerization reaction is a primary step in the process of the present invention.

Typically, a dehydrocyclodimerization reaction is carried out at temperatures in excess of 500° F. using dual-function catalysts containing an acidic component and a dehydrogenation component. These catalysts include acidic amorphous aluminas which contain metal promoters. Recently, crystalline aliminosilicates have been successfully employed as dehydrocylodimerization catalysts. Crystalline aluminosilicates, which are generally referred to as zeolites, may be represented by the empirical formula $$M_{2/n}O \cdot Al_2O_3 \cdot xSiO_2 \cdot yH_2O,$$

in which n is the valence of M, M is an element of Group I or Group II of the Periodic Table such as sodium, potassium, magnesium, calcium, strontium, or barium, and x is equal to or greater than 2.

Zeolites have skeletal structures which are made up of three dimensional networks of $SiO_4$ and $AiO_4$ tetrahedra, corner linked to each other by shared oxygen atoms. Such zeolites include mordenite and the ZSM variety. In addition to the zeolite component, certain metal promoters and inorganic oxide matrices have been included in dehydrocyclodimerization catalyst formulations. Examples of inorganic oxides include silica, alumina, and mixtures thereof. Metal promoters, such as Group VIII or Group III metals of the Periodic Table, have been used to provide the dehydrogenation functionality. The acidic function can be supplied by the inorganic oxide matrix, the zeolite, or both.

Molecular hydrogen is produced in a dehydrocyclodimerization reaction, as well as aromatic hydrocarbons. For example, reacting a $C_4$ paraffin will yield 5 moles of hydrogen for every mole of aromatic produced. Because the equilibrium concentration of aromatics is inversely proportional to the fifth power of the hydrogen concentration, it is desired to carry out the reaction in the absence of added hydrogen. However, the absence of hydrogen promotes rapid catalyst deactivation, which is caused by carbon formation (coking) on the catalyst surface. This relatively rapid coke deposition makes it necessary to more frequently perform the costly and time-consuming catalyst regeneration procedure. Reducing catalyst coking, thereby increasing catalyst time in service before regeneration is necessary, is an object of this invention.

There are several basic process schemes by which catalyst may be regenerated. Catalyst in the reaction zone may be maintained in continuous use over an extended period of time, from about five months to about a year or more, depending on the quality of the catalyst and the nature of the feedstock. Following the extended period of operation, the reactor, or reactors, must be taken out of service while the catalyst is regenerated or replaced with fresh catalyst. Of course, this necessitates shutdown of the hydrocarbon conversion unit.

In another process scheme, known as the swing reactor method, catalyst is regenerated with greater frequency. A multiple fixed bed reactor system is arranged for serial flow of feedstock in such a manner that one reactor at a time can be taken off-stream while the catalyst in that reactor is regenerated or replaced with fresh catalyst. The reactor with fresh catalyst is placed on-stream when another reactor is taken off-stream for the catalyst bed to be regenerated or replaced with fresh catalyst.

In another process scheme, a moving bed reaction zone and regeneration zone are employed. Fresh catalyst particles are supplied to a reaction zone, which may be comprised of several sub-zones, and the particles flow through the zone by gravity. Catalyst is withdrawn from the bottom of the reaction zone and transported to a regeneration zone where a multi-step process is used to recondition the catalyst to restore its full reaction-promoting ability. Catalyst flows by gravity through the various regeneration steps and then is withdrawn from the regeneration zone and supplied to the reaction zone.

Movement of catalyst through the zones is often referred to as continuous though, in practice, it is semi-continuous. By semi-continuous movement is meant the repeated transfer of relatively small amounts of catalyst at closely spaced points in time. For example, one batch per minute may be withdrawn from the bottom of a reaction zone and withdrawal may take one-half minute, that is, catalyst will flow for one-half minute. If the inventory in the reaction zone is large, the catalyst bed may be considered to be continuously moving. This method of operation is preferred by many of those skilled in the art. When the moving bed method is used, there is no loss of production while catalyst is removed and replaced. Also, use of the moving bed method avoids the shutdown and startup procedures of the swing reactor system relating to insertion and removal of a reactor in the process stream.

Catalyst regeneration is preferably accomplished in a moving bed mode, where catalyst is passed through various treatment zones, rather than practicing the several regeneration stages in a fixed bed of catalyst. Catalyst is passed downwardly through a regeneration vessel by gravity, where it is contacted with a hot oxygen-containing gas stream (known as recycle gas) in order to remove coke which accumulates on surfaces of the catalyst while it is in a hydrocarbon conversion reaction zone. Coke is comprised primarily of carbon but is also comprised of a relatively small quantity of hydrogen. The mechanism of coke removal is oxidation to carbon monoxide, carbon dioxide, and water. The coke content of spent catalyst may be as much as 20% of the catalyst weight, though 5 to 7% is a more typical amount.

After passing through a combustion zone, catalyst is passed into a drying zone for removal of water formed in the combustion zone which has remained on the catalyst instead of being carried off with combustion gases. Water removal is accomplished by passing a hot dry air stream through the catalyst. In some cases, catalyst leaving a combustion zone is passed through a halogenation zone before it is dried. Catalyst is usually passed out of the regeneration vessel after drying is accomplished. It is then subjected to additional treatment steps in order to complete the total regeneration process.

A hot dry air stream is introduced into the bottom of the regeneration vessel and flows upward, countercurrent to catalyst flow. After passing through the catalyst drying zone to accomplish removal of water, the air stream passes into the gas collection portion of the combustion zone, where it mixes with gases produced by combustion and inert gases which have passed through the combustion zone catalyst. This mixture, termed flue gas, is withdrawn from the combustion zone and at least a portion of it is mixed with air and recycled back to the combustion zone to contact the catalyst to effect coke burn-off. The portion which is not recycled is simply vented to atmosphere. In an alternate method, the air stream leaving the drying zone will have a sufficient oxygen concentration, so that it is not necessary to add more air. Also, the air stream leaving the drying zone may first be passed, in whole or in part, through a halogenation zone.

INFORMATION DISCLOSURE

The prior art recognizes numerous catalyst formulations for the conversion of aliphatic hydrocarbons into aromatic hydrocarbons. Of these catalyst formulations, none embody all of the aspects of the catalytic composition of the present invention nor is it apparent that these prior catalyst formulations have the unique coking tolerance which is characteristic of catalysts of the instant invention. A review of selected prior catalyst formulations may be found in U.S. Pat. No. 4,654,455, which is related to this application.

U.S. Pat. Nos. 4,600,700 (McHale), 4,463,209 (Kursewicz et al.), and 4,225,419 (Myers) deal with catalyst regeneration procedures in which water is beneficial.

U.S. Pat. Nos. 4,477,582 (Miale) and 4,642,407 (Dessau et al.) teach methods of regeneration of steam-deactivated catalysts.

Figure 2:
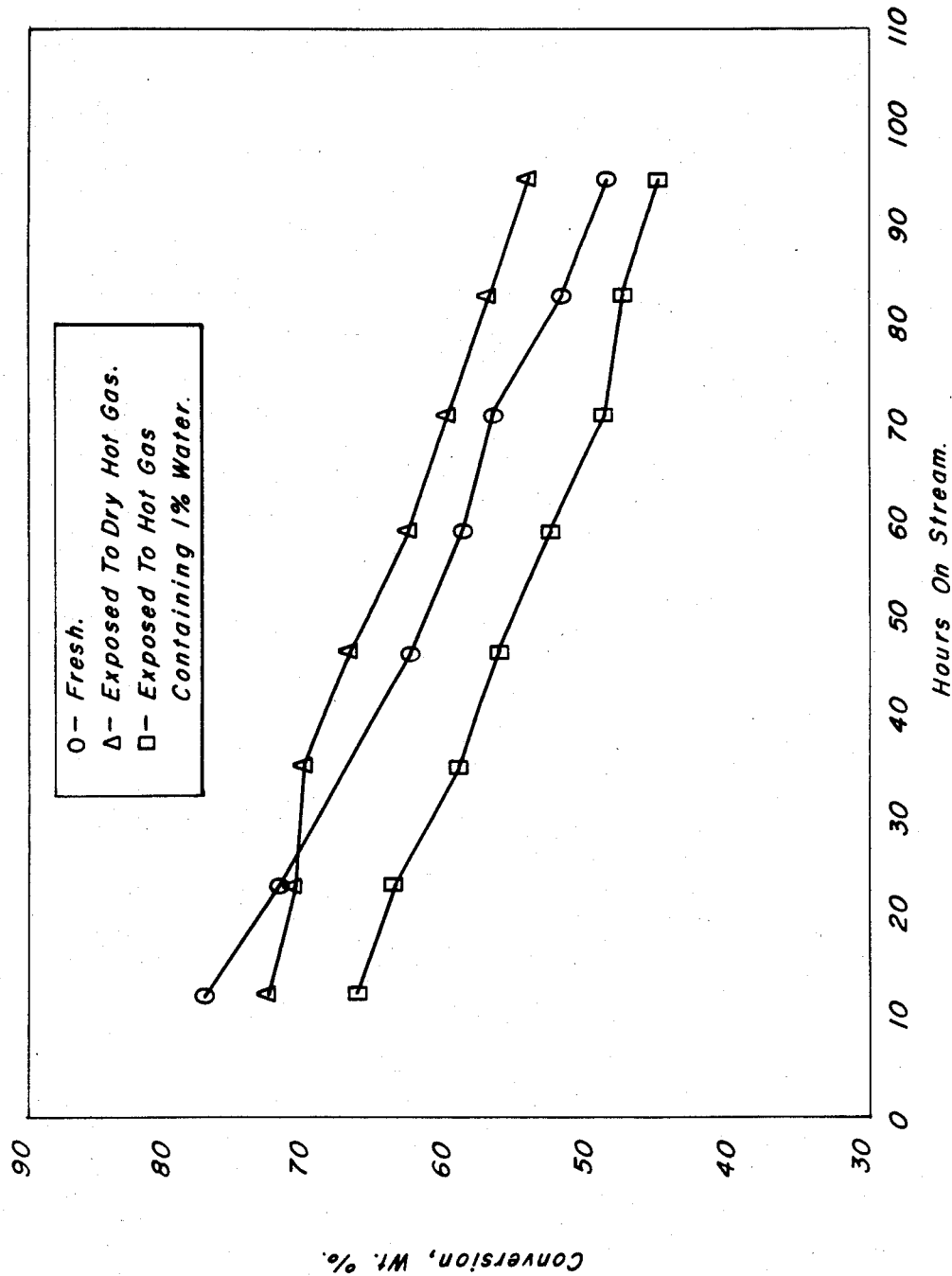
Figure 3:
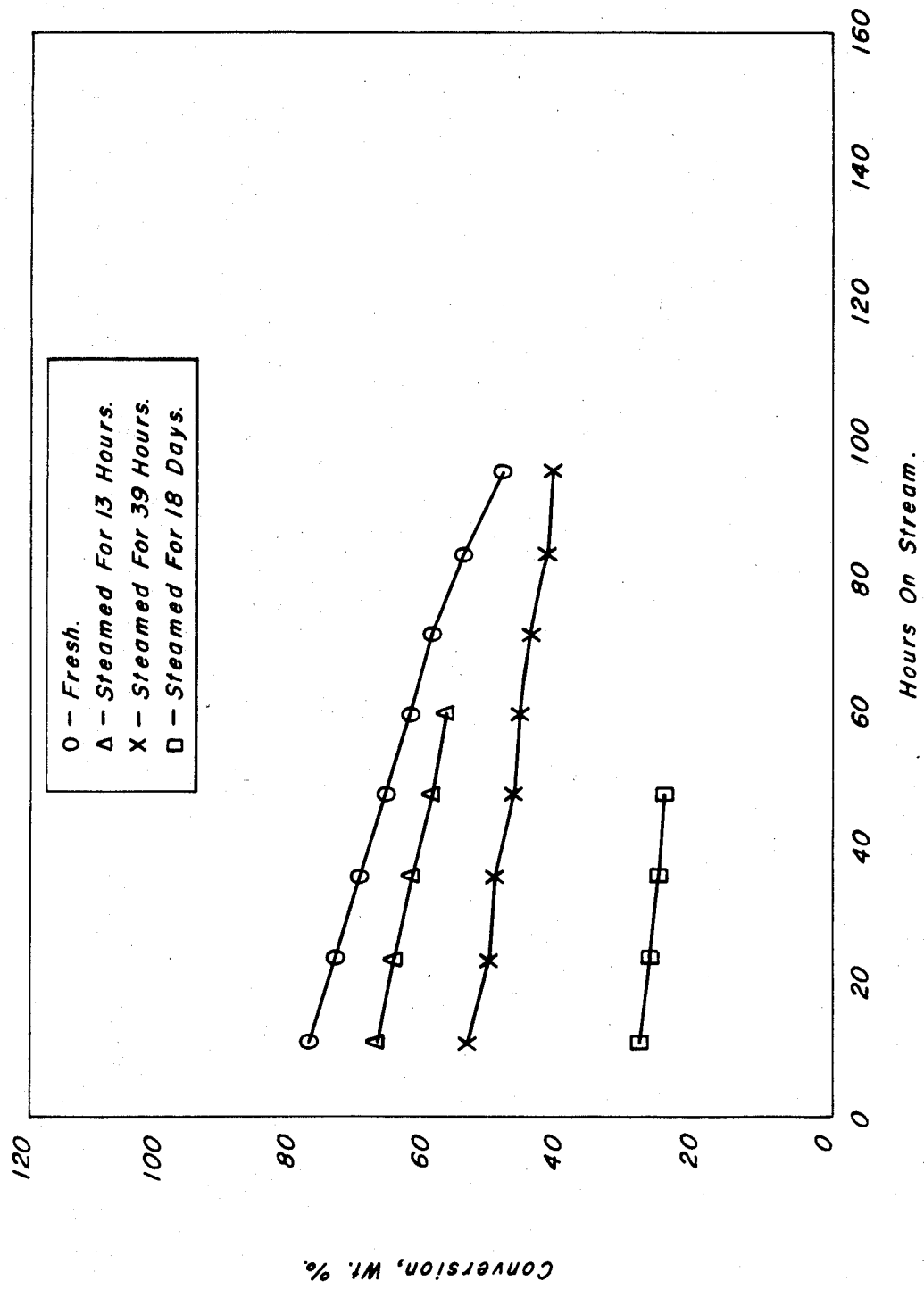

The curves of FIGS. 2 and 3 show the effect of catalyst exposure to water at high temperatures.

DETAILED DESCRIPTION OF THE INVENTION

This invention deals with the dehydrocyclodimerization of aliphatic hydrocarbons utilizing a novel catalytic composition comprising phosphorus-containing alumina, a gallium component, and crystalline aluminosilicate having a silica to alumina ratio of at least 12. This catalytic composite yields more aromatics, has a longer life expectancy, and cokes less than conventional dehydrocyclodimerization catalysts of the prior art. The lower coking tendency increases the economic attractiveness of the dehydrocyclodimerization process by requiring fewer catalyst regeneration cycles and increasing the on-stream efficiency, thereby increasing the production of aromatics.

It is believed that the presence of phosphorus-containing alumina is directly responsible for the observed reduced catalyst coke levels. The phosphorus may be combined with the alumina in any acceptable manner known to those skilled in the art. The amount of phosphorus in the catalytic composite can vary over a wide range. A phosphorous to aluminum ratio ranging from about 1:1 to about 1:100 is preferred. A 1:1 molar ratio corresponds to a phosphorus-containing alumina containing 20.5 wt % aluminum and 24.7 wt % phosphorus, while a 1:100 ratio corresponds to 0.6 wt % phosphorus and 52.0 wt % aluminum.

Representative phosphorus-containing compounds which may be utilized in the present invention include $H_3PO_4$, $H_3PO_2$, $H_3PO_3$, $(NH_4)H_2PO_4$, $(NH_4)_2HPO_4$, $K_3PO_4$, $K_2HPO_4$, $KH_2PO_4$, $Na_3PO_4$, $Na_2HPO_4$, $NaH_2PO_4$, $PX_3$, $RPX_2$, $R_2PX$, $R_3P$, $X_3PO$, $(XO)_3PO$, $(XO)_3P$, $R_3PO$, $R_3PS$, $RPO_2$, $RPS_2$, $RP(O)(OX_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as a phenyl radical, and X is hydrogen, R, or a halide. The alkyl groups preferably contain one to four carbon atoms.

Also, primary ($RPH_2$), secondary ($R_2PH$), and tertiary ($R_3P$) phosphines such as butyl phosphine, the tertiary phosphine oxides ($R_3PO$) such as tributylphosphine oxide, the tertiary phosphine sulfides ($R_3PS$), the primary $[RP(O)(OX)_2]$ and secondary $[R_2P(O)OX]$ phosphonic acids such as benzene phosphonic acid, the corresponding sulfur derivatives such as $RP(S)(SX)_2$ and $R_2P(S)SX$, the esters of the phosphonic acids such as dialkyl phosphonate $[(RO)_2P(O)H]$, dialkyl alkyl phosphonates $[(RO)_2P(O)R]$, and alkyl dialkyl-phosphinates $[(RO)P(O)R_2]$, phosphinous acids, $(R_2POX)$ such as diethylphosphinous acid, primary $[(RO)P(OX)_2]$, secondary $[(RO)_2POX]$, and tertiary $[(RO)_3P]$ phosphites and esters thereof, such as the monopropyl ester, alkyl dialkylphosphinites $[(RO)PR_2]$, and dialkyl alkylphosphinite, $[(RO)_2PR]$ esters.

Also, corresponding sulfur derivatives such as $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Also, phosphite esters, such as trimethylphosphite, triethylphosphite, diisopropylphosphite, and butylphosphite. Also, pyrophosphites such as tetraethylpyrophosphite.

Also, ammonium hydrogen phosphate, the phosphorus halides such as phosphorus trichloride, alkyl phosphorodichloridites $[(RO)PCl_2]$, dialkylphosphorochloridites $[(RO)_2PCl]$, dialkylphosphinochloridites $(RO_2PCl)$, alkyl alkylphosphonochloridates $[(RO)(R)P(O)Cl]$, dialkylphosphinochloridates $[R_2P(O)Cl$ and $RP(O)Cl_2]$. Also, corresponding sulfur derivatives such as $(RS)PCl_2$, $(RS)_2PCl$, $(RS)(R)P(S)Cl$, and $R_2P(S)Cl$.

The catalytic composite of the instant invention may be manufactured by any of several techniques known to those skilled in the art. Spheres are a particularly useful shape of the catalytic composite and may be formed by the well-known oil drop method. An exemplary method of manufacture comprises forming an alumina hydrosol by any of the techniques taught in the art, preferably by reacting aluminum metal with aqueous hydrochloric acid, combining the alumina hydrosol with crystalline aluminosilicate zeolite, mixing the resultant alumina zeolite hydrosol with a phosphorus-containing compound, adding a suitable gelling agent, then dispersing droplets of the mixture into an oil bath maintained at an elevated temperature. The droplets of the mixture remain in the oil bath until they set and form hydrogel spheres. The spheres are then withdrawn from the oil bath and typically subjected to an aging, or curing treatment in oil. In a particular process variation, the spheres may be cured in an ammonical solution to further improve their physical characteristics. The aged particles are washed in water, dried at a temperature of about 150° to about 205° C., and subjected to a calcination procedure at a temperature of about 450° C. to about 700° C. for a period of about 1 to about 24 hours. This treatment effects conversion of the hydrogel spheres to the desired phosphorus-containing alumina composite. Then gallium is added and a second calcining step is carried out. U.S. Pat. No. 2,620,314 may be consulted for additional information.

The alumina hydrosol is typically prepared by digesting aluminum in aqueous hydrochloric acid and/or aluminum chloride solution at a temperature of from about 80° to about 105° C. The chloride compound concentration of the resulting aluminum chloride solution is reduced by maintaining an excess of aluminum in the reaction mixture. The alumina hydrosol is an aluminum chloride hydrosol which may be, for example, an aluminum oxychloride hydrosol or aluminum hydroxychloride hydrosol. The aluminum chloride hydrosol is prepared with an aluminum to chloride ratio from about 0.70:1 to about 1.5:1 by weight. The crystalline aluminosilicate zeolite is combined with the alumina sol.

The gelling agent is typically a weak base which, when mixed with the hydrosol, will cause the mixture to set to a gel within a reasonable time. Ammonia is often used. Usually, the ammonia is furnished by an ammonia precursor which is added to the hydrosol. The precursor may be hexamethylenetetramine, urea, or mixtures thereof. Other weak basic materials which are substantially stable at normal temperatures but decompose to form ammonia with increasing temperature may be used.

During the above-mentioned aging process, residual ammonia precursor retained in the spheroidal particles continues to hydrolyze and effect further polymerization of the hydrogel, whereby desirable pore characteristics are established. Aging of the hydrogel is accomplished over a period from about 1 to about 24 hours, preferably in an oil suspending medium, at a temperature of from about 60° to about 150° C. or more, and at a pressure to maintain the water content of the hydrogel spheres in a substantially liquid phase. The aging of the hydrogel can also be carried out in aqueous $NH_3$ solution at about 95° C. for a period up to about 6 hours. Following the aging step the hydrogel spheres may be washed with water containing ammonia.

It may be desirable that, as known to those skilled in the art, the phosphorus-containing alumina of the present invention contain minor amounts of other inorganic oxides such as titanium dioxide, zirconium dioxide, tin oxide, germanium oxide, chromium oxide, beryllium oxide, vanadium oxide, cesium oxide, hafnium oxide, zinc oxide, iron oxide, cobalt oxide, magnesia, boria, thoria, and the like. These materials may be added to the mixture prior to oil-dropping.

The catalytic composite of the present invention contains a gallium component, which may be present in any form, including the elemental metal, oxide, hydroxide, halide, oxyhalide, aluminate, or which may be in chemical combination with one or more of the other ingredients of the catalytic composite. Although it is not intended to restrict the present invention by this explanation, it is believed that the best results are obtained when the gallium component is present in the composite in the zero valency state. The gallium component can be used in any amount which is catalytically effective with good results obtained, on an elemental basis, with about 0.1 to about 5% gallium by weight of the total catalytic composite. Best results are ordinarily achieved with about 0.5 to 1 wt % gallium. Although not a necessary condition of the present invention, it is believed that a substantial portion of the gallium present in the catalyst composite is located in and/or on the crystalline aluminosilicate component.

Gallium may be incorporated into the catalytic composite in any suitable manner known to the art which results in a relatively uniform dispersion of the gallium, such as ion exchange, co-gelation, or impregnation either after, before, or during the compositing of the catalyst formulation. It is intended to include within the scope of the present invention all conventional methods for incorporating and simultaneously uniformly distributing a metallic component in a catalytic composite. The particular method of incorporation used is not deemed to be an essential feature of the present invention. A preferred method of incorporating the gallium involves ion exchange of the crystalline aluminosilicate with a soluble decomposable compound of gallium, such as gallium tribromide, gallium perchlorate, gallium trichloride, gallium hydroxide, gallium nitrates, gallium oxalate, and the like.

Crystalline aluminosilicate zeolites with silica to alumina ratios of at least 12 are used in the present catalytic composite. A preferred zeolite group is known as the ZSM variety. It is most preferred that ZSM-5 be utilized as the crystalline aluminosilicate component of the present invention, but ZSM-8, ZSM-11, ZSM-12, and ZSM-35 may be used. These ZSM type zeolites are generally prepared by crystallizing a mixture containing a source of alumina, a source of silica, a source of alkali metal, water, and a tetraalkylammonium compound or its precursors. Of course, other crystalline aluminosilicates which meet the silica to alumina ratio criteria may be used, such as faujasites, L-type, mordenites, omega-type, and the like. The relative proportions of the crystalline alumino-silicate zeolite and the other components of the catalytic composite vary widely, with the zeolite content ranging from about 40 percent to about 80 percent by weight and more preferably in the range from about 50 to 70 percent by weight of composite.

The dehydrocyclodimerization conditions which are employed with the catalyst composition of the present invention will vary, depending on such factors as feedstock composition and desired conversion. A range of conditions for the dehydrocyclodimerization of $C_2$–$C_5$ aliphatic hydrocarbons to aromatics includes a temperature from about 350° C. to about 650° C., a pressure from about 1 to about 20 atmospheres, and a liquid hourly space velocity from about 0.2 to about 5 $hr^{-1}$. The preferred process conditions are a temperature in the range from about 400° to about 550° C., a pressure in the range of from about 2 to about 10 atmospheres and a liquid hourly space velocity of between 0.5 to 2.0 $hr^{-1}$. A temperature in the lower end of the range is required for optimum performance when the average carbon number of the feed stream is relatively high and as the average carbon number of the feed decreases the required temperature for optimum conversion increases.

The feed stream to the dehydrocyclodimerization process is comprised of $C_2$–$C_5$ aliphatic hydrocarbon, that is, open, straight, or branched chain hydrocarbons having two, three, four or five carbon atoms per molecule. The hydrocarbons may be saturated or unsaturated. Preferably, the feed stream is comprised of one or more of the following: isobutane, normal butane, isobutene, normal butene, propane, and propylene. The feed stream is contacted with the instant catalytic composite in a reaction zone maintained at dehydrocyclodimerization conditions. The reaction zone may be a fixed bed system or a moving bed system. The catalyst composite of the present invention may be used with a dehydrocyclodimerization catalyst of the prior art in a two-catalyst system.

The feed stream is preheated by any suitable heating means to the desired reaction temperature and then passed into a dehydrocyclodimerization reaction zone containing one or more beds of the instant catalytic composite. The reaction zone may comprise one or more separate reactors with suitable means therebetween to assure that the desired conversion temperature is maintained at the entrance to each reactor. Reactants may be contacted with a catalyst bed in either upward, downward, or radial flow fashion, with the latter being preferred. The reactants may be in the liquid phase, admixed liquid-vapor phase, or a vapor phase when they contact the catalyst, with the best results obtained in the vapor phase. In a multiple bed system, the present catalyst composite may be used in less than all of the beds, with another dehydrocyclodimerization catalyst being used in the remainder of the beds. In a dense-phase moving bed system, catalyst is removed from the bottom of the reaction zone, regenerated, and then returned to the top of the reaction zone.

The following example and experimental results are presented to teach one of the methods of preparation of the present catalyst and to show its superior tolerance to coking. This example should not, however, be construed as limiting the scope of the invention as set forth in the claims.

Catalyst A was made in the following manner. A first solution was prepared by adding phosphoric acid to an aqueous solution of hexamethylenetetramine (HMT) in an amount to yield a phosphorus content of the finished catalyst equal to about 8 wt %. A second solution was prepared by adding a ZSM-5 type zeolite to enough alumina sol, which was prepared by digesting metallic aluminum in hydrochloric acid, to yield a zeolite content in the finished catalyst equal to about 67 wt %. These two solutions were mixed to yield a homogenous admixture of HMT, phosphorus, alumina sol, and zeolite. This admixture was dispersed as droplets into an oil bath maintained at about 93° C. The droplets remained in the oil bath until they set and formed hydrogel spheres. The spheres were removed from the oil bath, water-washed, air-dried, and calcined at a temperature of about 482° C. A solution of gallium nitrate was utilized to impregnate the spheres to achieve a gallium content on the finished catalyst equal to about 1 wt %. After impregnation the spheres were calcined a second time, in the presence of steam, at a temperature of about 649° C.

A second catalyst, designated as Catalyst B, was prepared in substantially the same manner as Catalyst A, but without the phosphorus compound.

Catalysts A and B were tested using identical reactors and operating conditions and a feed to the reactors consisting of 85% n-$C_4$ and 15% i-$C_4$. The operating conditions were: reactor pressure of about 6.0 atmospheres absolute, liquid hourly space velocity of 2 $hr^{-1}$, and reactor inlet temperature of about 538° C. Conversion of the feed, selectivity for aromatic compounds, and catalyst carbon content were measured after 100 hours of operation. The Table presents the results.

Carbon content is the amount of carbon on the catalyst divided by the amount of catalyst and carbon. Conversion and selectivity are averages, since they are based on analyses of the total product collected during the run. Conversion is expressed in accordance with the commonly-used convention, that is, $C_3+C_4$ conversion. This means that the conversion is based on both propane and butanes (plus small amounts of propylene and butylenes) in the product. Of course, butane conversion is much higher, about 99%. Selectivity is the amount of aromatics divided by the conversion.

TABLE

|  | P wt % | Selectivity wt % | Conversion wt % | Carbon wt. % |
|---|---|---|---|---|
| Catalyst A | 8 | 57 | 45 | 5.8 |
| Catalyst B | 0 | 54 | 45 | 30.5 |

Though the conversions and selectivities are nearly equal, there is more than a five-fold difference in coke content (measured as carbon). This clearly illustrates that a catalyst composite made in accordance with the present invention possesses a much higher tolerance to coking than does a catalyst made in a conventional manner.

Figure 1:
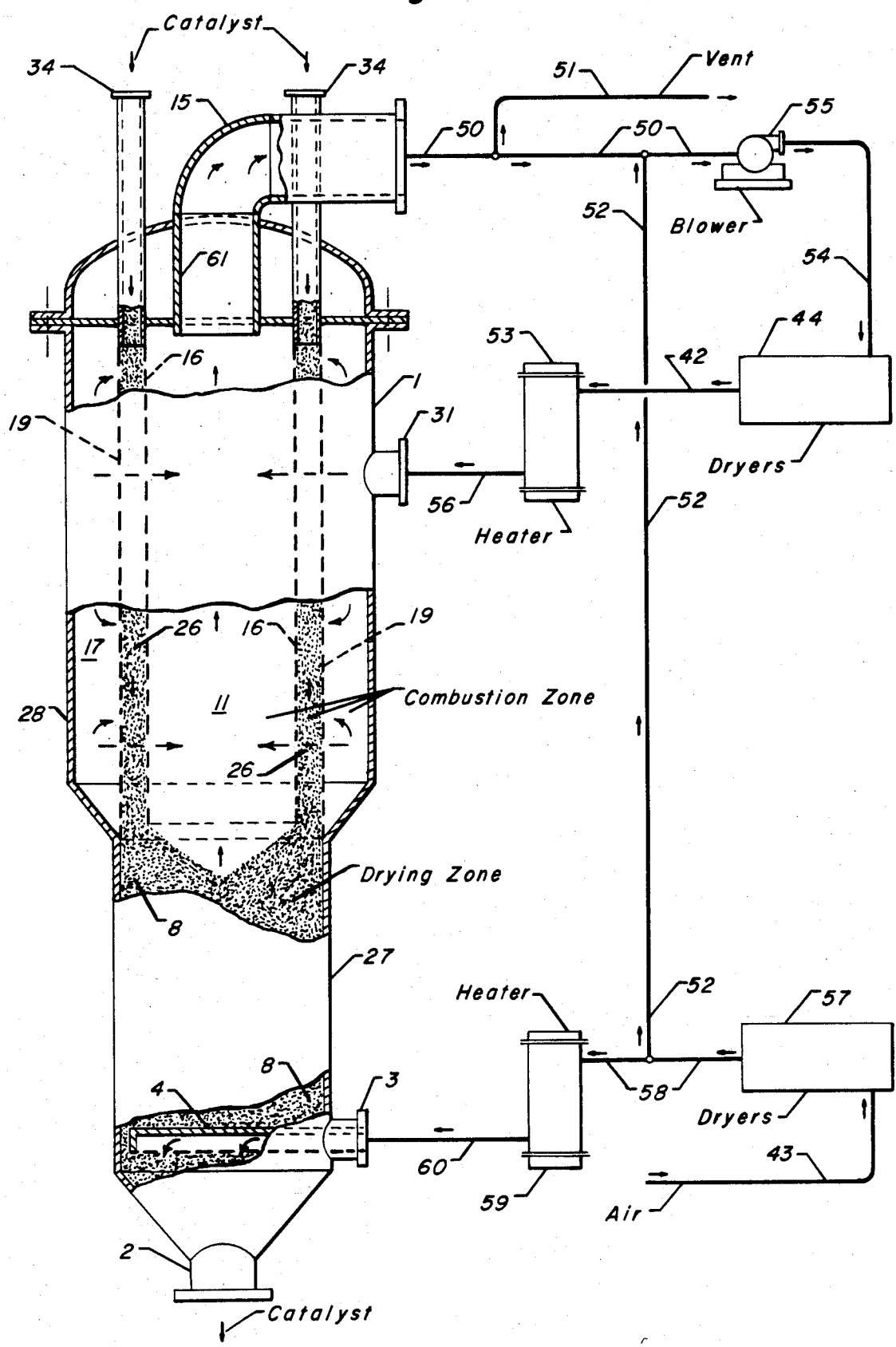
FIG. 1 is a schematic representation depicting a catalyst regeneration vessel and associated equipment which may be used in a catalyst regeneration process. The cutaway portions result from passing a vertical section plane along the vertical centerline of the vessel to divide the vessel in half. Elements not relevant to the present invention have been omitted.

FIG. 1 will now be utilized in describing the catalyst regeneration procedure; such use is not intended to limit the broad scope of the invention as presented in the claims. The Drawing shows only elements and equipment which are essential to a clear understanding of the invention. Application and use of additional required items is well within the purview of one skilled in the art. U.S. Pat. Nos. 3,652,231, 3,647,680 and 3,692,496 may be consulted for additional detailed information on catalyst regeneration.

Referring now to FIG. 1, spent catalyst particles are introduced into regeneration vessel 1 by means of nozzles 34. Though two catalyst inlet nozzles are shown, only one nozzle or multiple nozzles may be utilized. Catalyst is removed from regenerator 1 at the lower end, through nozzle 2. Regenerator 1 has an upper section 28, in which coke is burned, and a lower section 27, in which catalyst is dried.

There are two catalyst retention screens 16 and 19 within the upper section 28 of regeneration vessel 1. Both of the catalyst retention screens are cylindrical in form and have as their central axis the central axis of the regeneration vessel and are concentrically disposed in the upper section of the regeneration vessel. Screens 16 and 19 form a catalyst retention space through which a descending annular column 26, or bed 26, of catalyst moves by gravity. Catalyst inlet conduits which are downward extensions of nozzles 34 deliver catalyst at points spaced around the annular bed. The catalyst screens have openings sufficiently small to preclude catalyst particles from passing through the screens. For a description of catalyst retention means, U.S. Pat. No. 3,652,231 may be consulted. The catalyst retention screens extend throughout the upper section of vessel 1 and discharge catalyst to the lower section 27 of regenerator 1.

The upper section of vessel 1 is termed the burn zone, or combustion zone, where combustion of coke takes place. A space which serves to distribute recycle gas around the catalyst bed is formed between catalyst retention screen 19 and the sidewall of the upper section 28 of regeneration vessel 1. Recycle gas enters the gas distribution space, denoted by reference number 17, by means of recycle gas nozzle 31.

Recycle gas flows radially, or horizontally, from gas distribution space 17 through the catalyst retained between screens 16 and 19 to a central space 11, which is termed the flue gas collection space. Conduit 61 is an extension of flue gas outlet nozzle 15 within the vessel and conduit 61 is in communication with gas collection space 11.

Screen 19 extends into the lower section 27 of vessel 1, which is of a smaller diameter than the upper section, as can be seen in FIG. 1. The outside diameter of screen 19 at its lower end is slightly smaller than the inside diameter of the chamber lower section and the screen projects a short distance into the lower section. Catalyst discharged from the annular space between the catalyst retention screens fills all of lower section 27 of vessel 1. Catalyst moves downward through the lower section of the vessel and out of the vessel by means of catalyst outlet nozzle 2.

Nozzle 3 of regeneration vessel 1 is equipped with means for distributing air 4 to various points in a horizontal plane which is perpendicular to the descending catalyst, so that air will flow uniformly up to the column in contact with all of the catalyst 8 in lower section 27, which may be denoted the drying zone. The means for distributing air depicted in FIG. 2 is a perforated pipe extending into the vessel via nozzle 3 and held in place by a flange bolted to the flange of nozzle 3. A more elaborate arrangement of perforated pipes may be used or other means for distributing air may be used.

Air drawn from the atmosphere by a blower (not shown) passes through pipeline 43 and dryers 57, exiting the dryers in pipeline 58. A portion of the dry air stream is withdrawn from pipeline 58 via pipeline 52, while the balance is routed to heater 59. The dry hot air stream leaving heater 59 is conveyed to the regenerator vessel by pipeline 60.

Flue gas is withdrawn from the regeneration vessel in pipeline 50. A portion of the flue gas is vented to atmosphere via pipeline 51 and the balance of the flue gas is combined with the stream of dried air from pipeline 52. In an alternative arrangement, the air added to pipeline 50 upstream of blower 55 may not be dried prior to addition. The combined stream, now termed recycle gas, is increased in pressure by blower 55 and conveyed to dryers 44 by pipeline 54. The dried recycle gas is conveyed from the dryers to heater 53 via pipeline 42. Hot dry recycle gas is then supplied to the combustion zone by means of pipeline 56.

FIG. 2 depicts the results of testing done on three catalyst samples which were prepared in accordance with the present invention. Each of the three samples was placed in a pilot plant reaction vessel and held there under the test conditions for 18 days. One of the samples was exposed to a flow of dry hot gas at 490° Celsius and atmospheric pressure. The gas consisted of 99% nitrogen and 1% oxygen. A second sample was exposed to a gas stream consisting of 99% air and 1% steam at the same conditions of temperature and pressure. The relevant difference between these two gas streams is the water content; that the amounts of oxygen and nitrogen are different is irrelevant. The third sample, which is termed fresh catalyst, remained at room temperature and was not exposed to steam.

After 18 days, each of the samples was tested for catalytic activity at dehydrocyclodimerization conditions. The feed stream to each reactor consisted of 99.9 wt. % propane, with the balance being isobutane. Samples were taken at intervals, as shown in FIG. 2. $C_3+C_4$ conversion is plotted against time in service. It can be seen from FIG. 2 that exposing the catalyst to steam reduces its ability to catalyze the hydrocarbon conversion reaction.

FIG. 3 depicts the results of testing done on four catalyst samples which were taken from a batch of catalyst prepared in accordance with the present invention. Two samples were exposed to 11 mol. % steam in air at 548° C., one for 13 hours and one for 39 hours. One sample was exposed to the same concentration of steam at 490° C. for 18 days. One sample was not exposed to steam.

Aromatization tests were run using a feed stream consisting of 99.9 mol. % propane and 0.1 mol. % isobutane. The tests were run at 15 psig (approximately 2 atmospheres absolute), 0.8 $hr^{-1}$ LHSV, and 540° C. inlet temperature. FIG. 3 shows the $C_3+C_4$ conversion obtained by analyzing samples taken at various intervals. It can be seen from the four curves that activity decreases as time of exposure to steam increases. Of course, activity also decreases with time on stream. Testing of the catalyst sample which was exposed to steam for 18 days was halted early because its activity was so low.

Fresh and steamed catalysts were analyzed for pore volume and surface area by both nitrogen adsorption and mercury intrusion. There were no observable differences between the steamed and fresh samples. The zeolite Si/Al ratio as determined by MAS-NMR (magic angle spinning-nuclear magnetic resonance), was increased by a factor of five by steaming a catalyst sample. This clearly indicates that dealumination caused by steaming is responsible for the decreased activities of catalyst samples contacted with water at elevated temperatures.

Many types of equipment for removing water from an air stream are known to those skilled in the art. A preferred method for use in the present invention is adsorption on a molecular sieve. A dry air stream of the present invention will contain less than 100 wppm of water and, preferably, less than 10 wppm.

What is claimed:

1. A process for the dehydrocyclodimerization of hydrocarbons which comprises contacting a feed stream containing aliphatic hydrocarbons with a catalyst, under dehydrocyclodimerization conditions, where said catalyst is comprised of phosphorus-containing alumina, a gallium component, and a crystalline aluminosilicate having a silica to alumina ratio of at least 12, where said catalyst becomes deactivated as a result of the dehydrocyclodimerization reaction, and where water is excluded from contact with said catalyst during catalyst regeneration, the catalyst regeneration procedure being comprised of the steps of:
   (a) passing spent catalyst through a combustion zone which is maintained at a coke-oxidizing temperature, wherein said spent catalyst is contacted with a dry recycle gas comprising oxygen;
   (b) withdrawing a flue gas stream from the combustion zone;
   (c) mixing an air stream with said flue gas stream to form said recycle gas stream;
   (d) passing the recycle gas stream through a drying zone wherein water is removed from the recycle gas stream; and,
   (e) passing the dry recycle gas stream through the catalyst in the combustion zone.

2. A process for the dehydrocyclodimerization of hydrocarbons which comprises contacting a feed stream containing aliphatic hydrocarbons with a catalyst, under dehydrocyclodimerization conditions, where said catalyst is comprised of phosphorus-containing alumina, a gallium component, and a crystalline aluminosilicate having a silica to alumina ratio of at least 12, where said catalyst becomes deactivated as a result of the dehydrocyclodimerization reaction, and where water is excluded from contact with said catalyst during catalyst regeneration, the catalyst regeneration procedure being comprised of the steps of:
   (a) passing spent catalyst through a combustion zone which is maintained at a coke-oxidizing temperature, wherein said spent catalyst is contacted with a dry recycle gas comprising oxygen;
   (b) passing catalyst leaving said combustion zone through a catalyst drying zone wherein water is removed from the catalyst;
   (c) passing a first air stream through an air drying zone wherein water is removed from said first air stream and heating said first air stream;
   (d) passing at least a portion of said heated and dried first air stream through said catalyst drying zone in contact with catalyst, thereby removing water from the catalyst;
   (e) mixing at least a portion of the air stream leaving the catalyst drying zone with a gas stream leaving the catalyst bed in the combustion zone to form a flue gas stream;
   (f) mixing a second air stream with said flue gas stream to form said recycle gas stream;

(g) passing the recycle gas stream through a drying zone wherein water is removed from the recycle gas stream; and, (h) passing the dry recycle gas stream through the catalyst in the combustion zone.

3. The process of claim 2 wherein a portion of said flue gas stream is vented to atmosphere.

4. The process of claim 2 wherein said second air stream is a portion of said heated and dried first air stream.

* * * * *